United States Patent [19]

Ong et al.

[11] Patent Number: 4,853,308
[45] Date of Patent: Aug. 1, 1989

[54] PHOTORESPONSIVE IMAGING MEMBERS WITH FLUORENE HOLE TRANSPORTING LAYERS

[75] Inventors: Beng S. Ong, Mississauga; John R. C. Fuller, Oakville; Dasarao K. Murti, Mississauga, all of Canada

[73] Assignee: Xerox Corporation, Stamford, Conn.

[21] Appl. No.: 118,677

[22] Filed: Nov. 9, 1987

[51] Int. Cl.⁴ .......................................... G03G 15/02
[52] U.S. Cl. ......................................... 430/59; 430/72; 430/73
[58] Field of Search ............................. 430/59, 72, 73

[56] References Cited

U.S. PATENT DOCUMENTS

| | | |
|---|---|---|
| 3,307,940 | 3/1967 | Hoegl et al. |
| 3,615,412 | 10/1971 | Hessel . |
| 3,767,393 | 10/1973 | Fox ................................. 430/72 X |
| 4,046,564 | 9/1977 | Turner ................................. 430/72 |
| 4,106,934 | 8/1978 | Turnblom . |
| 4,245,021 | 1/1981 | Kazami et al. ........................ 430/58 |
| 4,400,455 | 8/1983 | Hashimoto et al. .................. 430/59 |
| 4,407,919 | 10/1983 | Murayama et al. .................. 430/58 |
| 4,415,640 | 11/1983 | Goto et al. ............................ 430/59 |
| 4,559,287 | 12/1985 | McAnency et al. .................. 430/59 |
| 4,562,132 | 12/1985 | Ong et al. ............................. 430/59 |

FOREIGN PATENT DOCUMENTS

| | | | |
|---|---|---|---|
| 56-22437 | 3/1981 | Japan | 430/72 |
| 57-102652 | 6/1982 | Japan | 430/59 |

Primary Examiner—Roland E. Martin
Attorney, Agent, or Firm—E. O. Palazzo

[57] ABSTRACT

A layered photoresponsive imaging member comprised of a supporting substrate, a photogenerating layer, and a hole transport layer comprised of novel bis(-diarylamino)fluorenes of the formula:

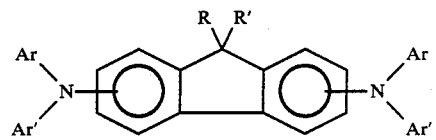

where R and R' are independently selected from the group consisting of hydrogen, alkyl, and substituted alkyl groups; and Ar and Ar' are independently selected from the group consisting of aryl and substituted aryl substituents.

32 Claims, 1 Drawing Sheet

PHOTORESPONSIVE IMAGING MEMBERS WITH FLUORENE HOLE TRANSPORTING LAYERS

BACKGROUND OF THE INVENTION

This invention is generally directed to photoresponsive imaging members, and more specifically the present invention is directed to layered photoresponsive imaging members with a hole transporting layer comprised of certain fluorenes. Thus, in one embodiment the present invention relates to an imaging member comrprised of a photogenerating layer, and a hole transport layer comprised of bis(diarylamino)fluroenes Further, in another embodiment of the present invention there is provided an imaging member comprised of a supporting substrate, a hole transport layer comprised of bis(diarylamino)fluorenes, and situated therebetween a photogenerating layer. Additionally, the present invention includes within the scope thereof imaging members wherein the photogenerating layer is situated between the hole transporting layer, and the supporting substrate. The photoresponsive imaging members of the present invention are useful for incorporation into various imaging systems, particularly xerographic imaging processes wherein, for example, the members are initially charged negatively, and development is accomplished by dry or liquid developer compositions. Also, the aforementioned fluorene derivatives of the present invention possess superior hole transport properties and can be economically prepared. Furthermore, the layered photoresponsive imaging members of the present invention are durable and are insensitive to changes in environmental conditions such as humidity and temperature.

The generation and development of electrostatic latent images on the surfaces of photoconductive materials by electrostatic means is well known. One electrostatic method involves the formation of a latent image on the surface of a photoreceptor. The photoreceptors can be comprised of a conductive substrate containing on its surface a layer of photoconductive insulating material, and in many instances there can be incorporated therein a thin barrier layer between the substrate and the photoconductive layer to prevent charge injection into the photoconductive layer upon charging of its surface, which injection would adversely effect the quality of the resulting image.

Numerous different xerographic photoconductive members are known including, for example, a homogeneous layer of a single material such as vitreous selenium, which can function as both a photogenerating and hole transporting substance, or composite layered devices, with a photoconductive substance dispersed in other substances. An example of one type of composite photoconductive layer used in xerography is discribed, for example, in U.S. Pat. No. 3,121,006 wherein there is disclosed a number of layers comprising finely divided particles of a photoconductive inorganic compound dispersed in an electrically insulating organic resin binder.

There are also known photoreceptor materials comprised of other inorganic materials wherein the charge carrier generation and charge carrier transport functions are accomplished by discrete contiguous layers. Additionally, photoreceptors are disclosed in the prior art which include an overcoating layer of an electrically insulating polymeric material, and in conjunction with this overcoated type photoreceptor there have been proposed a number of imaging methods. However, the art of xerography continues to advance and more stringent demands need to be met by the copying apparatus for increased performance. Additionally, positively charged layered photoresponsive imaging members are needed for generating images of acceptable resolution, and substantially no undesirable background deposits.

Recently, there has been disclosed layered photoresponsive devices comprised of generating layers and aryl amine hole transport layers, reference U.S. Pat. No. 4,265,990, the disclosure of which is totally incorporated herein by reference. Examples of generating layers disclosed in these patents include trigonal selenium and phthalocyanines, while examples of the active transport layer molecules that may be employed are comprised of the aryl amines illustrated therein. The imaging members of the present invention are similar to those described in the aforementioned patent with the primary exception that there are selected in place of the aryl amines the fluorene derivatives illustrated herein, which fluorenes possess improved characteristics, including permitting the more rapid transport of holes. Furthermore, the fluorene hole transport molecules of the present invention possess excellent compatibility with common polymer binders such as polycarbonates, polyesters, poly(methyl methacrylate), polystyrene copolymers, and the like, thus ensuring excellent long-term stability of the transport layers. Moreover, the fluorene derivative hole transport compounds selected for the imaging members of the present invention can be economically obtained by simple synthetic processes, and wherein the products resulting are of exceptionally high purity thus enabling them to be very suitable for xerographic imaging methods.

Other representative prior art disclosing layered photoresponsive devices include U.S. Pat. Nos. 4,115,116; 4,047,949; 4,081,274 and 4,315,981. According to the disclosure of the U.S. Pat. No. 4,315,981, the recording member consists of an electroconductive support, a photoconductive layer of organic materials which contain a charge carrier producing dyestuff layer of a compound having an aromatic, or heterocyclic polynuclear quinone ring system, and a charge transport layer.

Furthermore, there is disclosed in U.S. Pat. No. 4,135,928 electrophotographic light sensitive members comprised of 7-nitro-2-aza-9-fluorenylidene-malononitrile as charge transporting substances. According to the disclosure of this patent, the electrographic light sensitive members are comprised of an electroconductive support, a layer thereover of a photogenerating substance, and 7-nitro-2-aza-9-fluorenylidene-malononitrile of the formula, for example, as illustrated in column 1. There are also disclosed in U.S. Pat. No. 4,474,865 imaging members with electron transporting layers of fluorenylidene derivatives. In addition, there are also known layered photoresponsive imaging members wherein there are selected hole transport layers of aryl amines, and various photogenerating squaraine compounds, reference for example U.S. Pat. Nos. 4,552,822; 4,415,639; 4,471,041; and 4,486,520

There are also illustrated in U.S. Pat. No. 4,618,551, the disclosure of which is totally incorporated herein by reference, photoresponsive imaging members with photogenerating layers, and charge transport layers comprised of polysilylenes. More specifically, there is illustrated in the aforementioned patent a polysilylene hole transporting compound for use in imaging members, which compound is of the formula as illustrated in claim 1 with specific examples of polysilylenes being poly(methylphenylsiylene) of an average molecular weight of greater than 50,000.

Also of particular interest is U.S. Pat. No. 4,106,934, which illustrates photoconductive insulating compositions containing one or more p-type organic photoconductor components and a charge transfer complex of one or more electron acceceptor components of the formulas as illustrated in the Abstract, for example. Particularly useful as Formula 1 type compounds are those materials as illustrated in column 5, beginning at line 30. Further, the use of N-substituted polymeric acrylic acid amides and alpha-alkyl acid amides as overcoatings for photoconductors is illustrated in U.S. Pat. No. 3,307,940 (see Formula 5, column 2). Moreover, fluorenylidene derivatives as charge transporting compounds in photoreceptors are disclosed in U.S. Pat. Nos. 4,400,455; 4,245,021; 4,415,640; 4,559,287 and 4,562,132. In addition U.S. Pat. No. 3,615,412 discloses organic photoconductors with certain fluorenes fused to benzo and naphtho ring structures, reference columns 1 to 3.

In addition, of interest is copending application U.S. Ser. No. 061,247, filed June 2, 1987, which illustrates imaging members with hydroxy fluorene derivatives, which derivatives are similar to those of the present invention with the exception that they contain thereon two hydroxy groups. Other copending applications filed June 1987, and disclosing imaging members with fluorene polymers are U.S. Ser. Nos. 061,064; 061,052; 061,248 and 061,053.

Although imaging members with various hole transporting substances, including aryl amines and polysilylenes, are suitable for intended purposes, there continues to be a need for the development of improved members, particularly layered members which are comprised of aminofluroene transport layers; and which members are insensitive to the changes in environmental conditions. Moreover, there continues to be a need for specific layered imaging members which not only generate acceptable images, but which can be repeatedly used in a number of imaging cycles without deterioration thereof from the machine environment or surrounding conditions. Additionally, there continues to be a need for improved layered imaging members wherein the materials employed for the respective layers, particularly the hole transporting layer, are substantially inert to the users of these members. Further, there continues to be a need for improved photoresponsive imaging members which can be prepared with a minimum number of processing steps, and wherein the layers are sufficiently adhered to one another to allow the continuous use of these imaging members in repetitive imaging processes. Also, there continues to be a need for new hole transporting compounds that, when dispersed in polymeric matrices, are also useful as protective overcoating layers, and as interface materials for various imaging members. There also is a need for new hole transporting substances which enable increased mobility of holes in layered imaging members. Likewise, there is a need for hole transporting layers with increased stability, for example, wherein there is essentially no bleeding and segregation or crystallization of the transport molecules from the layers after extended usage. Furthermore, there is a need for hole transporting compounds useful in layered imaging members, which compounds are superior insulators in the dark compared to many other known hole transporting compounds, thus enabling charging of the resulting imaging member to higher fields while maintaining cyclic stability, and allowing improved developability. Additionally, there is a need for enabling the preparation of imaging members with new hole transporting compounds wherein the preparation allows for the selection of a variety of solvents, inclusive of toluene, benzene, tetrahydrofuran, cyclohexane, and halogenated solvents in addition to methylene chloride. There is also a need for imaging members with improved electrical characteristics, and comprised of fluorene hole transporting compounds, which members can be positively or negatively charged depending on the configuration of the member. Another need of the present invention resides in the provision of a novel class of fluorene hole transport molecules whose physical, electrical and electrochemical properties can be modified by altering the two carbon-9 substituents. Moreover, there continues to be a need for a simple synthetic process for the preparation of fluorene hole transporting compounds useful in the layered imaging members of the present invention.

SUMMARY OF THE INVENTION

It is, therefore, an object of the present invention to provide an improved photoresponsive member with the above-noted advantages.

It is yet another object of the present invention to provide an improved photoresponsive imaging member with novel fluorene hole transporting compounds.

A further specific object of the present invention is the provision of an improved photoresponsive imaging member containing a photogenerating layer, and in contact therewith a hole transporting layer of fluorene compounds.

Another specific object of the present invention is the provision of an improved photoresponsive imaging member containing a photogenerating layer, and in contact therewith certain fluorenes as the hole transporting layer.

Yet another object of the present invention resides in the provision of an improved overcoated photoresponsive imaging member with a photogenerating composition layer situated between the hole transport layer and a supporting substrate.

In another object of the present invention there are provided processes for affecting preparation of the hole transporting compounds disclosed hereinafter.

In yet another object of the present invention there are provided imaging and printing methods, including xerographic processes, utilizing the improved photoresponsive imaging member of the present invention.

In still yet another object of the present invention there are provided hole transporting compounds which are compatible with common matrix binders, inclusive of polycarbonates, enabling the dispersion of these compounds to be maintained for extended time periods with or without the use of stabilizers.

Moreover, in another object of the present invention is the provision of novel hole transport compounds which are environmentally safe and inert to the users thereof.

A further object of the present invention is to provide novel fluorene hole transport layers whose electrical performance is insensitive to changes in environmental conditions.

These and other objects of the present invention are accomplished by the provision of an improved photoresponsive imaging member comprising a photogenerating layer and a hole transporting layer in contact therewith. More specifically, the present invention in one embodiment is directed to a photoresponsive imaging member comprised of a photogenerating layer situated between a fluorene hole transporting layer, and a supporting substrate.

The fluorene derivative hole transporting compounds selected for the present invention are represented by the following formula:

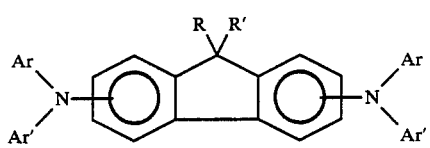

wherein R, and R' are independently selected from the group consisting of hydrogen, alkyl substituents, and substituted alkyl substituents; and Ar, and Ar' are independently selected from aromatic groups, such as those containing from about 6 to about 24 carbon atoms, from sustituted aromatic groups, or mixtures thereof.

Illustrative examples of alkyl groups include those of from about 1 carbon atom to about 25 carbon atoms, and preferabl6y of from 1 carbon atom to about 10 carbon atoms, such as methyl, ethyl, propyl, butyl, pentyl, hexyl, octyl, nonyl, decyl, pentadecyl, stearyl, and the like, with methyl, ethyl, propyl, and butyl being preferred. Aryl substituents include those of from 6 carbon atoms to about 24 carbon atoms, such as phenyl, tolyl and naphthyl. The alkyl groups can be substituted with alkoxy, hydroxy, holo, cyano, alkoxyalkyl, and the like. In addition, the aromatic groups can be substituted with alkyl, halo, and the like.

Examples of hole transporting compounds embraced within the present invention, and suitable for incorporation into the imaging members disclosed herein include 9,9-dimethyl-2,7-bis(phenyl-p-chlorophenylamino)fluorene; 9,9-dipropyl-2,7-bis(phenyl-m-tolylamino)-fluorene; 9-ethyl-9-propyl-2,7-bis(di-m-tolylamino)fluorene; 9,9-bis(2-cyanoethyl)-2,7-bis(phenyl-m-tolylamino)fluorene; 9,9-bis(3-hydroxypropyl)-2,7-bis(phenyl-m-tolylamino)fluorene; 9,9-bis([2-(methoxycarbonyl)-ethyl]-2,7-bis(phenyl-m-tolylamino; 9,9-bis[2-(ethoxycarbonyl)-ethyl]-2,7-bis(phenyl-m-chlorophenylamino)fluorene; 9,9-diethyl-2,7-bis[bis(m-chlorophenyl)amihno]fluorene; 9,9-dimethyl-2,5-bis(m-toly-m-chlorophenylamino)fluorene; 9,9-dibutyl-2,7-bis(diphenylamino)fluorene; 9,9-dibutyl-2,7-bis(di-m-tolylamino)fluorene, 9,9-bis(3-acetoxypropyl)-2,7-bis(-phenyl-m-tolylamino)fluorene, and the like.

The hole transporting compounds encompassed within the scope of the present invention are not commercially available but can be readily synthesized by the Ullmann condensation of a diarylamine with a sustituted diiodofluorene according to the following reaction scheme:

SCHEME:
PREPARATION OF BIS(DIARYLAMINO)FLUORENES

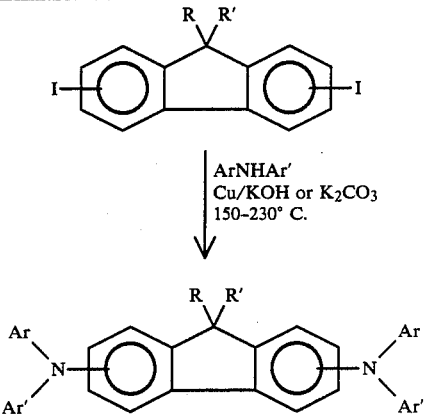

wherein R, R', Ar, and Ar' are as defined herein, and I is iodine atom

The diodofluorene precursor reactants can be obtained from substituted fluorenes by appropriate iodination reactions. For example, 9,9-bis(2-cyanoethyl)-2,7-diiodofluorene was synthesized from 9,9-bis(2-cyanoethyl)fluorene by iodinatin with a mixture of iodine and a strong oxidizing agent.

The improved photoresponsive imaging members of the present invention can be obtained by a number of known methods, the process parameters and the order of the coating of the layers being dependent on the member desired. Thus, for example, the improved photoresponsive imaging members of the present invention can be prepared by providing a conductive substrate containing an optional charge blocking layer, and an optional adhesive layer; and applying thereto by solvent coating processes, laminating processes, or other methods, a photogenerating layer and the hole transporting layer.

Further, the improved photoresponsive members of the present invention can be utilized in various imaging systems; and more importantly can function simultaneously in imaging and printing systems with visible light or infrared light, wherein the members are initially charged positively or negatively; followed by imagewise exposure; development of the image with a developer composition comprised of toner particles and carrier particles; transferring the developed image to a suitable substrate, such as paper; and permanently affixing the image thereon. The imaging members of the present invention are also useful for generating colored images subsequent to development with color toner compositions.

BRIEF DESCRIPTION OF THE DRAWINGS

For a better understanding of the present invention and further features thereof, reference is made to the following detailed description of various preferred embodiments wherein.

DESCRIPTION OF THE PREFERRED EMBODIMENTS

Figure 1:
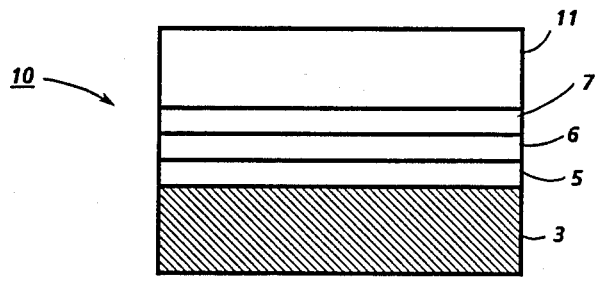
FIG. 1 is a partially schematic cross-sectional view of the improved photoresponsive imaging member of the present invention.

Illustrated in FIG. 1 is the improved photoresponsive imaging member of the present invention, generally designated 10; and comprising a substrate 3, an optional charge blocking layer 5, and adhesive layer 6, a charge carrier photogenerating layer 7, and a hole transporting layer 11 comprised of the fluorenes illustrated herein.

Figure 2:
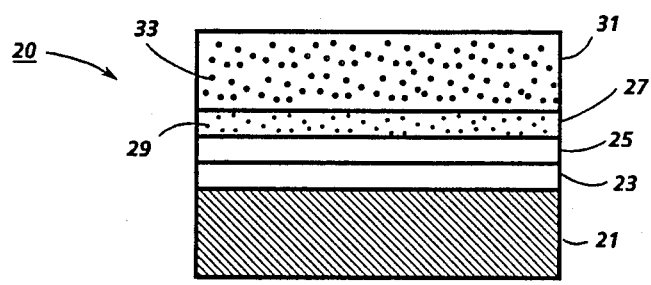
FIG. 2 is a partially schematic cross-sectional view of a second photoresponsive member of the present invention.

Illustrated in FIG. 2 is a second photoresponsive imaging member of the present invention, generally designated 20; and comprising a supporting substrate 21, an optional charge blocking layer 23, an adhesive layer 25, a charge carrier photogenerating layer 27 of trigonal slelenium or vanadyl phthalocyanine optionally dispersed in an active resinous binder 29, and a hole transporting layer 31, comprised of the fluorene hole transporting compounds of the present invention dispersed in an inactive resinous binder 33.

Figure 3:
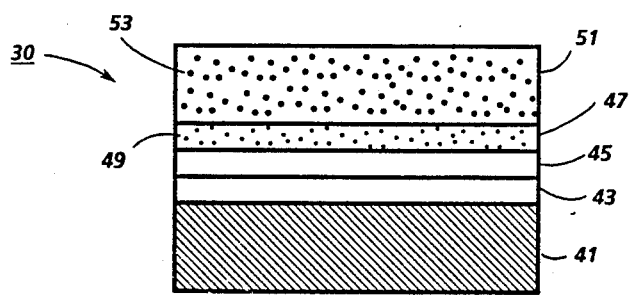
FIG. 3 illustrates a third photoresponsive imaging member of the present invention.

Illustrated in FIG. 3 is a preferred improved photoresponsive imaging member of the present invention, generally designated 30; and comprising a substrate 41, a charge blocking layer 43, an adhesive layer 45, a charge carrier photogenerating layer 47 of trigonal selenium, selenium alloys or vanadyl phthalocyanine, optionally dispersed in an inactive resinous binder 49, and a hole transporting layer 51, comprised of bis(-diarylamino)fluorene dispersed in an inactive resinous binder 53.

The supporting substrate layers may be opaque or transparent and may comprise any suitable marerial having the requisite mechanical properties. Therefore, the substrate may be comprised of a layer of nonconducting material such as an inorganic or organic polymeric material with a conductive surface layer arranged thereon, or a conductive material, inclusive of, for example, a metallized organic polymeric material, aluminum, chromium, nickel, indium, tin oxide, and brass. Also, the substrate may be flexible or rigid, and may have many different configurations such as, for example, a plate, a cylindrical drum, a scroll, and an endless belt.

The thickness of the substrate layer depends on many factors, including economical considerations, thus this layer may be of substantial thickness, for example, over 100 mils or of minimum thickness providing the objectives of the present invention are accomplished. In one preferred embodiment, the thickness of the supporting substrate is from about 1 mil to about 50 mils.

As optional charge blocking layers there can be selected various suitable known materials including aluminum oxide, polysilanes, and the like. The primary purpose of this layer is to provide charge blocking, that is to prevent charge injection from the substrate during and after charging. Generally, this layer has a thickness of less than 50 Angstroms. The adhesive layer is typically a polymeric material, including polyesters such as DuPont 49,000 polyester, and the like. Genrally, this layer has a thickness of about 0.1 micron.

Photogenerating layers can include therein known photoconductive charge carrier generating materials, such as amorphous selenium, selenium alloys, halogen doped amorphous selenium, halogen doped amorphous selenium alloys, trigonal selenium, selenite and carbonates with trigonal selenium, reference U.S. Pat. Nos. 4,232,102 and 4,233,283, the disclosures of which are totally incorporated herein by reference, copper and chlorine doped cadmium sulfide, cadmium selenide, and cadmium sulfur selenide, and the like. Alloys of selenium included within the scope of the present invention are selenium tellurium alloys, selenium arsenic alloys, and preferably such alloys containing a halogen, such as chlorine, in an amount of from about 50 to 200 parts per million. Other photogenerating layer pigments include metal phthalocyanines, metal free phthalocyanines, vanadyl phthalocyanines, other known phthalocyanines, reference U.S. Pat. No. 3,816,118, the disclosure of which is totally incorporated herein by reference, squarylium pigments, charge transfer complex materials, and various sensitizers such as cyanine dyes, and the like.

Typically, the photogenerating layer has a thickness of from about 0.05 micron to about 10 microns or more, and preferably is of a thickness of from about 0.4 micron to about 3 microns. Generally, however, the thickness of the photogenerating layer is dependent on the photogenerating pigment loading, which may vary from about 5 percent by volume to about 100 percent by volume, and other factors inclusive of mechanical considerations, for example, and whether a flexible photoresponsive imaging member is desired. Illustrative examples of polymeric binder resinous materials that can be selected for the photogenerating layer pigmets include those as disclosed, for example, in U.S. Pat. No. 3,121,006, the disclosure of which is totally incorporated herein by reference, polyesters, polycarbonate resins, polyvinyl carbazole, epoxy resins, phenoxy resins, and the like.

The hole transporting compounds of the present invention can also be dispersed in a resinous binder in an amount of from about 10 percent by weight to about 75 percent by weight, and preferably in an amount of from about 30 percent by weight to about 50 percent by weight. Illustrative examples of organic resinous material useful as a transport binder include polycarbonates, acrylate polymers, vinyl polymers, cellulose polymers, polyesters, polysiloxanes, polyamides, polyurethanes and epoxies, as well as block, random or alternating copolymers thereof. Preferred electrically inactive binder materials are polycarbonate resins having a molecular weight of from about 20,000 to about 100,000 with a molecular weight in the range of from about 50,000 to about 100,000 being particularly preferred. Also, this layer can be of various suitable thicknesses, and generally is of from about 5 microns to about 80 microns.

Furthermore, the imaging members of the present invention are particularly useful in electrophotographic, especially xerographic, imaging methods wherein negatively charged latent images are formed on the imaging member, subsequently affecting development of the image formed with a toner composition comprised of resin particles, pigment particles , and charge enhancing additives such as distearyl dimethyl ammonium methyl sulfate, thereafter transferring the image to a suitable substrate and permanently affixing the image thereto.

The invention will now be described in detail with respect to specific preferred embodiments thereof, it being understood that these examples are intended to be illustrative only. Also, the invention is not intended to be limited to the materials, conditions, and process parameters recited therein. All parts and percentages are by weight unless otherwise indicated.

EXAMPLE I

2,7-diiodo-9,9-bis(2-cyanoethyl)fluorene

A mixture of 27.2 grams of 9,9-bis(2-cyanoethyl)fluorene prepared according to the procedure published in *Journal of American Chemical Society*, Volume 64, page 2427, 1942, 27.8 grams of iodine, and 31.4 grams of ammonium persulfate was charged into a round-bottomed flask containing 200 milliliters of acetic acid, 10 milliliters of concentrated sulfuric acid, and 40 millilters of water. The mixure was stirred mechanically and heated at 80° C. for four hours. After the reaction, the reaction mixture was poured into water. The precipitated crude product was filtered, washed with water, and recrystallized from acetic acid to affort 40.5 grams of pure 2,7-diiodo-9,9-bis(2-cyanoethyl)fluorene, melting point, 262° 265° C.

Elemental Analysis: Calculated for $C_{19}H_{14}I_2N_2$: C, 43.54; H, 2.69; N, 5.34. Found: C, 43.12; H, 2.80; N, 5.31.

$^1$H NMR (CDCl$_3$), δ (ppm): 1.6(t, 4H); 2.4(t, 4H); 7.2 to 8.0(m, 6H).

IR (KBr pellet): 2,240 cm$^{-1}$.

MS, m/e (relative intensity): 524(100); 470(50); 430(35); 398(37); 344(38); 304(14); 215(12); 189(15); 176(42).

EXAMPLE II

9,9-bis(2-cyanoethyl)-2,7-bis(phenyl-m-tolylamino)fluorene

A mixture of 5.0 grams of 2,7-diiodo-9,9-bis(2-cyanoethyl)fluorene as obtained above, 1.5 grams of copper bronze powder, and 10 milliliters of Soltrol ® 220 was stirred at room temperature in a dry round-bottomed flask under nitrogen atmosphere. After five minutes, 4.5 grams of potassium carbonate was added, and the mixture was heated to 150° C. before 5.2 grams of molten N-phenyl-m-toluidine was added. The resulting mixture was then heated under reflux at 210° C. for 24 hours. Thereafter, the reaction mixture was filtered while still hot, and the solid residue was washed several times with hot cyclohexane. The combined filtrate was evaporated under reduced pressure to yield a brown solid. Subsequently, the brown solid was dissolved in 250 milliliters of isopropanol, treated with decolorizing charcoal, and filtered. Concentrating the filtrate, followed by cooling, yielded white crystals of pure 9,9-bis(2-cyanoethyl)-2,7(phenyl-m-tolylamino)fluorene. The yield was 68 percent, melting point, 204° to 206° C.

Elemental Analysis: Calculated for $C_{45}H_{38}N_4$: C, 85.14; H, 6.03; N, 8.83. Found: C, 85.44; H, 5.98; N, 8.81.

$^1$H NMR (CDCL$_3$), δ (ppm): 1.7(t, 4H); 2.15(t, 4H); 2.25(s, 6H); 6.8 to 7.6(m, 24H).

IR (KBr pellet): 2,255 cm$^{-1}$.

MS, m/e (relative intensity): 634(100); 581(5); 540(38); 317(47); 270(50).

EXAMPLE III

2,7-diiodo-9,9bis[2-(methoxycarbonyl)ethyl]fluorene

Five hundred and fifty (550) milliliters of concentrated sulfuric acid was added slowly to 700 millilters of water in a 3-liter round-bottomed flask cooled with an ice bath, followed by stirring with a mechanical stirrer. To this aqueous acid solution was added in small portions 168 grams of 9,9-bis(2-cyanoethyl)fluorene. The resulting mixture was then heated under reflux for three hours. After reaction completion, the precipitated white solid product was filtered, washed several times with water, and recrystallized from isopropanol to yield 161 grams of pure 9,9-bis(2-carboxyethyl)fluorene.

Subsequently, 56 grams of 9,9-bis(2-carboxyethyl)fluorene as obtained above was added to a mixture of 46 grams of iodine and 41 grams of ammonium persulfate in a mixture of 11 milliliters of concentrated sulfuric acid, 50 milliliters of water, and 240 millilters of acetic acid. The resulting mixture was stirred mechanically, and heated at 80°for 12 hours. Thereafter, the precipitated white solid product, 2,7-diiodo-9,9-bis(2-carboxyethyl)fluorene, was filtered fron the hot reaction mixture, washed several times with water, and dried in vacuo at 65° C. overnight.

A mixture of the diacid as obtained above, and 600 milliliters of methanol was heated under reflux in the presence of 0.5 gram of concentrated sulfuric acid. After three hours, the reaction mixture was cooled to room temperature, and poured carefully into a swirling aqueous sodium bicarbonate solution. The precipitated diester was filtered, and washed three times with water. Recrystallization from a methanol and water mixture afforded 70 grams of pure, 99.5 percent, 2,7-diiodo-9,9-bis[2-(methoxycarbonyl)-ethylfluorene, melting point, 106° to 107.5° C.

Elemental Analysis: Calculated for $C_{21}H_{20}I_2O_4$: C, 42.74; H, 3.42; L O, 10.84. Found: C, 42.98; H, 3.53; O, 10.59.

Hu $^1$H NMR (CDCL$_3$), δ (ppm): 1.4(t, 4H); 2.3(t, 4H); 3.55(s, 6H); 7.4 to 8.0(m, 6H).

IR (KBr Pellet): 1,735 cm$^{-1}$.

MS, m/e (relative intensity): 590(82); 559L(3); 527(3); 503(6); 443(35); 376(37); 334(6); 316(25); 202(14); 189(100); 176(28).

EXAMPLE IV

9,9-bis[2-(methoxycarbonyl)ethyl]-2,7-bis(phenyl-m-tolylamino)fluorene

A mixture of 17.9 grams of 2,7-diiodo-9,9-bis[2-(methoxycarbonyl)ethyl]fluorene, 4.3 grams of copper bronze, 12.5 grams of potassium carbonate in 30 milliliters of Soltrol$^R$ 220 was mechanically stirred and heated to 150° C. under a nitrogen atmosphere. Fifteen (15.0) grams of molten N-phenyl-m-toluidine was then added dropwise at 150° C. After addition, the resulting mixture was heated at 210° C. under reflux for 24 hours. The hot reaction mixture was filtered, and the filter cake was washed several times with hot cyclohexane. Subsequently, the combined filtrate was evaporated under reduced pressure to yield a brown residue, which was purified by column chromatography on silica gel to afford 15.2 grams of pure 9,9-bis[2-(methoxycarbonyl)ethyl]-2,7bis(phenyl-m-tolylamino)fluorene, melting point, 159° to 160° C.

Elemental Analysis: Calculated for $C_{47}H_{44}N_2O_4$: C, 80.54; H, 6.33; O, 9.13. Found: C, 80.77; H, 6.65; O, 9.08.

$^1$H NMR (CDCl$_3$), δ (ppm): 1.7(t, 4H); 2.15(t, 4H); 2.25(s, 6H); 3.55(s, 6H); 6.8 to 7.5(m, 24H).

IR (KBr Pellet): 1,740 cm$^{-1}$.

MS, m/e (relative intensity): 614(2); 540(38); 519(20); 485(4); 431(32); 372(10); 350(100); 270(50); 262(30); 231(11); 223(15); 216(12); 186(11); 167(21).

EXAMPLE V

9,9-bis(3-hydroxypropyl)-2,7-bis(phenyl-m-tolylamino)fluorene

To a well-stirred solution of 8.8 grams of 9,9-bis[2-(methoxycarbonyl)ethyl]-2,7-bis(phenyl-m-tolylamino)- fluorene in 150 milliliters of dried tetrahydrofuran under a nitrogen atmosphere was added in small portions, 0.52 gram, of lithium aluminum hydride over a period of 15 to 30 minutes. The reaction mixture was stirred at room temperature for two hous. Ten percent aqueous sodium hydroxide solution was then slowly added to the reaction mixture. The organic layer was separated and evaporated to dryness under reduced pressure. The residue as dissolved in methylene chloride, and washed several times with water. Evaporation of the dry methylene chloride solution provided a white solid, which was recrystallized from isopropanol and water to yield 7.8 grams of the above fluorene pure product, melting point, 216° to 217° C.

Elemental Analysis Calculated for $C_{45}H_{44}N_2O_2$: C, 83.82; H, 6.88; O, 4.96. Found: C, 83.61; H, 6.93; O, 4.91.

$^1H$ NMR ($CD_2Cl_2$), δ (ppm): 0.95(m, 4H); 1.3(br s, 2H); 1.85(m, 4H); 2.25(s, 6H)); 3.3(t,4H); 6.8–7.6(m, 24H).

IR (KBr Pellet): 3,390 cm$^1$.

MS, m/e (relative intensity): 644(88); 540(20); 403(27); 385(19); 372(3); 357(4); 322(100); 270(33); 254(2); 216(3); 182(12); 167(25).

EXAMPLE VI

A layered photoresponsive imaging member comprised of the transport molecule, 9,9-bis(2-cyanoethyl)-2,7-bis(phenyl-m-tolylamino)fluorene synthesized in accordance with Example II, in a polycarbonate resinous binder as the hole transport layer, and trigonal selenium as the photogenerator, was prepared as follows:

A dispersion of trigonal selenium and poly(N-vinylcarbazole) was prepared by ball milling 1.6 grams of trigonal selenium and 1.6 grams of poly(N-vinylcarbazole) in 14 milliliters each of tetrahydrofuran and toluene. Ten grams of the resulting slurry was then diluted with a solution of 0.25 gram of 9,9-bis(2-cyanoethyl)-2,7-bis(phenyl-m-tolylamino)fluorene in 5 milliliters each of tetrahydrofuran and toluene. A 1.5 micron thick photogenerator layer was fabricated by coating the above dispersion onto an aluminized Mylar substrate, thickness of 2 mils, with a Bird Film applicator, followed by drying in a forced air oven at 135° C. for 5 minutes. A solution for the hole transport layer was then prepared by dissolving 1.0 gram of 9,9-bis(2-cyanoethyl)-2,7-bis(phenyl-m-tolylamino)fluorene of Example II and 1.0 gram of Makrolon polycarbonate in 14 millilitersa of methylene chloride. This solution was then coted over the photogenerator layer by means of a Bird Film applicator. The resulting member was then dried in a forced air oven at 130° C. for 30 minutes resulting in an 23 micron thick transport layer.

The fabricated imaging member was then electrically tested by negatively charging it with a corona, and discharged by exposing to white light of wavelengths of from 400 to 700 nanometers. Charging was accomplished with a single wire coroton in which the wire was contained in a grounded aluminum channel and was strung between two insulating blocks. The acceptance potential of this imaging member after charging, and its residual potential after exposure were recorded. The procedure was repeated for different exposure energies supplied by a 75 watt Xenon arc lamp of incident radiation, and the exposure energy required to discharge the surface potential of the member to half of its original value was determined. This surface potential was measured using a wire loop probe contained in a shielded cylinder, and placed directly above the photoreceptor member surface. This loop was capacitively coupled to the photoreceptor surface so that the voltage of the wire loop corresponded to the surface potential. Also, the cylinder enclosing the wire loop was connected to the ground.

For this imaging member, the acceptance potential was 1,100 volts, the residual potential was 75 volts, and the half decay exposure sensitivity was 2.5 ergs/cm$^2$. Further, the electrical properties of this photoreceptor member remained essentially unchanged for 1,000 cycles of repeated charging and discharging.

EXAMPLE VII

A layered photoresponsive imaging member with a transport layer of 9,9-bis(2-cyanoethyl)-2,7-bis(phenyl-m-tolyl-amino)fluorene in polycarbonate Z, and an amorphous selenium generator layer was fabricated as follows:

A 1 micron thick layer of amorphous selenium on a ball grained aluminum plate of a thickness of 7 mils was prepared by conventional vacuum deposition techniques. Vacuum deposition was accomplished at a vacuum of $10^{-6}$ Torr, while the substrate was maintained at about 50° C. A hole transport layer on top of the amorphous selenium layer was obtained by coating a solution of 50 percent by weight each of 9,9-bis(2-cyanoethyl)-2,7-bis(phenyl-m-tolylamino)fluorene, and polycarbonate Z in methylene chloride using a Bird Film applicator. This solution was prepared by dissolving 5 grams of 9,9-bis(2-cyanoethyl)-2,7-bis(phenyl-m-tolylamino)fluorene, and 5 grams of polycarbonate Z in 70 grams of methylene chloride. Thereafter, the resulting device was dried in a forced air oven at 50° C. for 2 hours to form a 17 micron thick transport layer. Subsequently, the imaging member was cooled to room temperature, followed by electrical testing in accordance with the procedure of Example VI except that a 450 nanometers monochromatic light was used for irradiation. Specifically, this imaging member was negatively charged to 950 volts and discharged to a residual potential of 60 volts. The half decay exposure sensitivity for this device was 2.5 ergs/cm$^2$.

EXAMPLE VIII

A layered photoresponsive imaging member comprised of 9,9-bis[2-(methoxycarbonyl)ethyl]-2,7-bis(phenyl-m-tolylamino)fluorene as obtained by the process of Example IV, and dispersed in Vitel PE-100 polyester (Goodyear) as the hole transport layer, and trigonal selenium as the photogenerator was fabricated as follows:

A 1 micron trigonal selenium photogenerator layer was prepared on an aluminized Mylar substrate in accordance with the procedure of Example VI. A solution for the transport layer was prepared by dissolving 5 grams of 9,9-bis[2-(methoxycarbonyl)ethyl]-2,7-bis(phenyl-m-tolylamino)fluorene and 13 grams of Vitel PE-100 polyester in 150 milliliters of methylene chloride, and 100 milliliters of 1,1,2-trichloroethane. Thereafer, the solution was spray coated on top of the photogenerator layer by means of a commercial spray gun in a spray booth at 20° C. and 35 percent relative humidity (R.H.. The resulting member was then dried in a forced air oven at 130° C. for 30 minutes resulting in a dry thickness for the transport layer of 20 microns. Electrical testing was carried out in accordance with the procedure of Example VI. For this imaging member, the acceptance potential was 1,000 volts, and the half decay exposure sensitivity was 3.0 ergs/cm².

EXAMPLE IX

A layered photoresponsive device comprised of 9,9-bis[2-(methoxycarbonyl)ethyl-2,7-bis(phenyl-m-tolylamino)fluorene as the transport molecule, and amorphous seleneium as the photogenerator, was fabricated as follows:

A 1 micron thick layer of amorphous selenium on a ball grained aluminum plate of a thickness of 5 mils was prepared in accordance with the procedure of Example VII. A hole transport layer on top of the amorphous selenium layer was obtained by coating a solution of 5 grams each of 9,9-bis[2-methoxycarbonyl)ethyl]-2,7-bis(phenyl-m-tolylamino)fluorene and poly(methyl methacrylate) in 40 ml milliliters of metylene chloride using a Bird Film applicator. Thereafter, the resulting device was dried in a forced air oven at 50° C. for 2 hours to form a 24 micron thick transport layer.

Electrical testing was affected by repeating the procedure of Example VII, and substantially similar results were achieved.

EXAMPLE X

A photoresponsive device comprised of 9,9-bis[2-(methoxycarbonyl)ethyl]-2,7-bis(phenyl-m-tolylamino)-fluorene as the transporting molecule, and squarylium pigments as the photogenerator was prepared as follows:

A ball grained aluminum substrate was coated with a solution of 1 milliliter of 3-aminopropyltrimethoxysilane in 100 milliliters of ethanol. the coating was heated at 110° C. for 10 minutes resulting in the formation of a 0.1 micron thick polysilane layer. A dispersion of a photogenerator prepared by ball milling a mixture of 0.075 gram of bis(N,N'-dimethylaminophenyl)squaraine and 0.13 gram of Vitel PE-200 polyester (Goodyear) in 12 milliliters of methylene chloride for 24 hours was then coated on top of the polysilane layer. After drying the coating in a forced air oven at 135° C. for 6 minutes, a 0.5 micron thick squarylium photogenerating layer was obtained.

A solution for the transport layer was then prepared by dissolving 1.0 gram each of 9,9-bis[2-(methoxycarbonyl)ethyl]-2,7-bis(phenyl-m-tolylamino)fluorene and Makrolon polycarbonate in 15 milliliters of methylene chloride. This solution was then coated over the above photogenerator layer using a Bird Film applicator. The resulting device was dried in a forced air oven at 135° C. for 30 minutes resulting in a 20 micron thick electron transport layer.

Electrical testing was affected in accordance with the procedure of Example VI. Specifically, the device was charged negatively to 1,050 volts, and discharged with 830 nanometers monochromatic light. For this imaging device, the half decay exposure sensitivity was 3.5 ergs/cm².

EXAMPLE XI

A photoresponsive imaging device with a spray coated transport layer comprised of 2,7-bis(di-m-tolylamino)-9,9-bis(3-hydroxypropyl)fluorene and a trigonal selenium photogenerator was fabricated as follows:

A 2 micron thick trigonal selenium photogenerator layer on an aluminized Mylar was prepared in accordance with the procedure of Example VIII. A solution for the transport layer was then prepared by dissolving 12 grams of 2,7-bis(di-m-tolylamino)-9,9-bis(3-hydroxypropyl)fluorene and 12 grams of Merlon polycarbonate in 150 milliliters of methylene chloride and 150 milliliters of 1,1,2-trichloroethane. This solution was spray coated over the photogenerator layer using a commercial spray gun in accordance with the procedure as described in Example VIII. The coating was dried in a forced air oven at 135° C. for 30 minutes yielding a transport layer of a thickness of 6 microns.

Electrical testing was affected by repeating the procedure of Example VIII, and substantially similar results were achieved.

EXAMPLE XII

A layered photoresponsive imaging member containing 9,9-bis(3-hydroxypropyl)-2,7-bis(phenyl-m-tolylamino)fluorene in a polycarbonate binder as the electron transport layer, and trigonal selenium as the photogenerator was prepared as follows:

A trigonal selenium photogenerator layer with a thickness of 2 microns was fabricated on an aluminized Mylar by repeating the procedure of Example VI. A solution for the transport layer was prepared by dissolving 1.0 gram each of 9,9-bis(3-hydroxypropyl)-2,7-bis(phenyl-m-tolylamino)fluorene and Merlon polycarbonate in 12 milliliters of methylene chloride. Thereafter, the solution was coated on top of the photogenerator layer by means of a Bird Film applicator. The resulting member was then dried in a forced air oven at 130° C. for 30 minutes resulting in a dry thickness of the transport layer of 18 microns.

Electrical testing was carried out in accordance with the procedure of Example VI. Specifically, this imaging member was negatively charged to 1,000 volts, and exposed to white light of wavelengths of 400 to 700 nanometers. The half decay exposure sensitivity of this device was 5.0 ergs/cm², and its electrical properties remained substantially the same after 1,000 cycles of repeated charging and discharging.

Other modifications of the present invention may occur to those skilled in the art based upon a reading of the present disclosure and these modifications are intended to be included within the scope of the present invention.

What is claimed is:

1. A layered photoresponsive imaging member comprised of a photogenerating layer and in contact therewith a hole transporting layer consisting essentially of fluorene derivatives of the following formula dispersed in an inactive resinous binder:

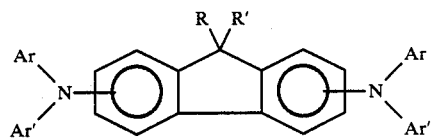

where R and R' are independently selected from the group consisting of hydrogen, alkyl, and substituted alkyl groups; and Ar and Ar' are independently selected from the group consisting of aryl and substituted aryl substituents.

2. An imaging member in accordance with claim 1 wherein R is an alkyl group of from 1 to about 20 carbon atoms.

3. An imaging member in accordance with claim 1 wherein R' is an alkyl group of from 1 to about 20 carbon atoms.

4. An imaging member in accordance with claim 1 wherein R is an alkyl group of from 1 to about 6 carbon atoms.

5. An imaging member in accordance with claim 1 wherein R' is an alkyl group of from 1 to about 6 carbon atoms.

6. An imaging member in accordance with claim 1 wherein Ar is an aromatic group with from about 6 to about 24 carbon atoms.

7. An imaging member in accordance with claim 1 wherein Ar' is an aromatic group of from about 6 to 24 carbon atoms.

8. An imaging member in accordance with claim 1 wherein the aryl substituents are phenyl.

9. An imaging member in accordance with claim 1 wherein the aryl substituents are tolyl.

10. An imaging member in accordance with claim 1 wherein the hole transporting compound is 9,9-bis(2-cyanoethyl)-2,7-bis(phenyl-m-tolylamino)fluorene.

11. An imaging member in accordance with claim 1 wherein the hole transporting compound is 9,9-bis[2-(methoxycarbonyl)ethyl]-2,7-bis(phenyl-m-tolyamino)fluorene.

12. An imaging member in accordance with claim 1 wherein the hole transporting compound is 9,9-bis(3-hydroxypropyl)-2,7-bis(phenyl-m-tolylamino)fluorene.

13. An imaging member in accordance with claim 1 wherein the hole transporting compound is 9,9-bis(2-cyanoethyl)-2,7-bis(di-m-tolylamino)fluorene.

14. An imaging member in accordance with claim 1 wherein the hole transporting compound is 9,9-dipropyl-2,7-bis(phenyl-p-tolylamino)fluorene.

15. An imaging member in accordance with claim 1 wherein the hole transporting compound is 9,9-dimethyl-2,7-bis(phenyl-p-chlorophenylamino)fluorene.

16. An imaging member in accordance with claim 1 wherein the hole transporting compound if 9-methyl-9-butyl-2,7-bis(di-m-chlorophenylamino(fluorene.

17. An imaging member in accordance with claim 1 wherein the hole transporting compound is 9,9-bis[2-(ethoxycarbonyl)ethyl]-2,7-bis(di-m-tolylamihno)fluorene.

18. An imaging member in accordance with claim 1 wherein the photogenerating compound is metal free phthalocyanines, metal phthalocyanines, vanadyl phthalocyanines, selenium, selenium alloys, or squararaine pigments.

19. An imaging member in accordance with claim 18 wherein the photogenerating compound is amorphous selenium, or trigonal selenium.

20. An imaging member in accordance with claim 18 wherein the photogenerating pigment is dispersed in a resinous binder.

21. An imaging member in accordance with claim 1 wherein the hole transporting compound is dispersed in a resinous binder in an amount of from about 25 to about 75 percent by weight.

22. An imaging member in accordance with claim 20 wherein the resinous binder is a polyester, a polycarbonate, an epoxy resin, a polyamide, a polysiloxane, or a vinyl polymer.

23. An imaging member in a accordance with claim 21 wherein the resinous binder is a polyester, a polycarbonate, an epoxy resin, a polyamide, a polysiloxane, or an vinyl polymer.

24. An imaging member in accordance with claim 1 containing a supporting substrate.

25. An imaging member in accordance with claim 24 wherein the supporting substrate is aluminum.

26. An imaging method which commprises generating an electrostatic latent image on the imaging member of claim 1, followed by developing this image, and subsequently transferring the image to a suitable substrate.

27. A method of imaging in accordance with claim 26 wherein the hole transporting compound is selected from the group consisting of 9,9bis(2-cyanoethyl)-2,7-bis(phenyl-m-tolylamino)fluorene; 9,9-bis[2-(methoxycarbonyl)ethyl]-2,7-bis(phenyl-m-tolyamino(fluorene; 9,9-bis(3-hydroxypropyl)-2,7-bis(phenyl-m-tolyamino)fluorene; 9,9-bis(2-cyanoethyl)-2,7-bis(di-m-tolylamino)fluorene; 9,9-dipropyl-2,7-bis(phenyl-p-tolylamino)fluorene; 9,9-dimethyl-2,7-bis(phenyl-p-chlorophenylamino)fluorene; 9,9-dimethyl-2,7-bis(phenyl-p-chlorophenylamino)fluorene; 9-methyl-9-butyl-2,7-bis(di-m-chlorophenylamino)fluorene; and 9,9-bis[2-(ethoxycarbonyl)ethyl]-2,7-bis(di-m-tolylamino)fluorene.

28. A printing method which comprises generating a latent image on the member of claim 1 with laser scanning, followed by developing this image, and subsequently tranferring the image of a suitable substrate.

29. An imaging member in accordance with claim 1 containing a charge blocking layer, and an adhesive layer.

30. An imaging member in accordance with claim 29 wherein R and R' are independently selected from the group consisting of alkyl groups of from 1 to about 20 carbon atoms.

31. An imaging member in accordance with claim 29 wherein R and R' are independently selected from the group conisting of alkyl groups of from 1 to about 6 carbon atoms.

32. An imaging member in accordance with claim 29 wherein Ar and Ar' are independently selected from the group consisting of aromatic groups with from about 6 to about 24 carbon atoms.

* * * * *